(12) United States Patent
Brion et al.

(10) Patent No.: US 10,773,575 B2
(45) Date of Patent: Sep. 15, 2020

(54) MULTIFUNCTIONAL MODULE FOR A PLUGGING AND SLIDING DOOR, AND VEHICLE THUS EQUIPPED

(71) Applicant: FAIVELEY TRANSPORT TOURS, Saint-Pierre-des-Corps (FR)

(72) Inventors: Florian Brion, Notre Dame D'oe (FR); Nicolas Pierre, Saint Regle (FR)

(73) Assignee: FAIVELEY TRANSPORT TOURS (FR)

( * ) Notice: Subject to any disclaimer, the term of this patent is extended or adjusted under 35 U.S.C. 154(b) by 153 days.

(21) Appl. No.: 15/850,929

(22) Filed: Dec. 21, 2017

(65) Prior Publication Data

US 2018/0178637 A1    Jun. 28, 2018

(30) Foreign Application Priority Data

Dec. 27, 2016   (FR) ...................................... 16 63400

(51) Int. Cl.
| | |
|---|---|
| *B60J 5/06* | (2006.01) |
| *E05F 15/632* | (2015.01) |
| *E05D 15/10* | (2006.01) |
| *E05F 15/657* | (2015.01) |

(52) U.S. Cl.
CPC .......... *B60J 5/062* (2013.01); *E05D 15/1007* (2013.01); *E05D 15/1068* (2013.01); *E05F 15/632* (2015.01); *E05F 15/657* (2015.01); *E05Y 2201/22* (2013.01); *E05Y 2201/638* (2013.01); *E05Y 2900/506* (2013.01); *E05Y 2900/51* (2013.01)

(58) Field of Classification Search
CPC .... E05D 15/1007; E05F 15/657; E05F 15/63; E05F 15/662; E05F 15/40; E05F 17/004; B60J 5/062; E05B 79/20
See application file for complete search history.

(56) References Cited

U.S. PATENT DOCUMENTS

| | | | | |
|---|---|---|---|---|
| 4,730,513 A * | 3/1988 | Heinrich | ................. | E05F 15/63 192/96 |
| 4,901,474 A * | 2/1990 | Bayard | ................. | E05F 15/565 292/144 |
| 5,263,280 A * | 11/1993 | Dilcher | ................ | B61D 19/009 49/212 |
| 5,332,279 A * | 7/1994 | Golemis | ................ | B60J 5/0497 192/69.6 |
| 8,997,401 B2 * | 4/2015 | Kowalczyk | ............. | E05D 15/54 49/326 |
| 9,869,118 B2 * | 1/2018 | Schmidt | ................ | E05F 15/657 |
| 2005/0132652 A1 * | 6/2005 | Tong | ........................ | B60J 5/062 49/334 |
| 2012/0291354 A1 * | 11/2012 | Giannis | .................... | E05F 15/63 49/324 |
| 2016/0046176 A1 * | 2/2016 | Prevost | ............... | E05D 15/1068 105/343 |
| 2016/0290027 A1 * | 10/2016 | Schmidt | ................ | E05F 15/657 |

* cited by examiner

*Primary Examiner* — Justin B Rephann
(74) *Attorney, Agent, or Firm* — Mary D. Lawlor; The Small Patent Law Group, LLC

(57) ABSTRACT

A multi-functional module for a plugging and sliding door of a vehicle, the door being moveable between open and closed positions.

17 Claims, 8 Drawing Sheets

MULTIFUNCTIONAL MODULE FOR A PLUGGING AND SLIDING DOOR, AND VEHICLE THUS EQUIPPED

CROSS-REFERENCE TO RELATED APPLICATIONS

The present application claims priority under 35 U.S.C. § 119 to French Patent Application No. FR 1663400 (filed on Dec. 27, 2016), which are each hereby incorporated by reference in their respective entirety.

TECHNICAL FIELD

Embodiments relate to the area of plugging and sliding doors for transport vehicles, and particularly, a public transport vehicle such as a train, a tram, or a trolley. Embodiments relate further to a module intended to equip such doors, which is to fulfill different functions connected to the implementation of these doors, and particularly, in case of emergency.

BACKGROUND

It is known to equip transport vehicles via plugging and sliding doors, of which the movement has an opening phase, wherein the movement forward of the panels along their suspension, in the direction of opening, is combined with a movement of the whole panel suspension, in the lateral direction towards the exterior of the vehicle. Then, when the lateral position is reached, the panels continue to move longitudinally until they reach the desired opening. This movement, carried out in the opposite direction to close the door, enables, and particularly, to ensure a perfect seal when the door is closed.

In the state of the art, it is provided to equip these plugging and sliding doors with mechanical devices, enabling to ensure various functionalities in case of emergency.

First, these doors are equipped with a device enabling an emergency opening function. In other words, the actuation of this device controls the forced opening of the door, and particularly, in case of perceiving a danger by users. To this end, a solution is known which calls upon an unlocking cable, likely to be actuated by a user using an emergency handle. The cable thus leads to a finger likely to unlock the locking mechanism triggered beforehand.

Moreover, these plugging and sliding doors are also provided with a device ensuring they are stopped from being actuated, and particularly, in the case of malfunctioning of the mechanical means dedicated for this purpose. Under these conditions, any movement of the door, from the close position thereof to the open position thereof, is prevented. This type of device can conventionally call upon an actuation body, generally positioned in the door panel, which prevents the plugging movement using a bolt inserted in a latch, itself fixed on the body of the vehicle.

In the state of the art, the two devices, respectively ensuring the emergency opening and that it is stopped from being actuated, are usually separate. Certainly, solutions are known, wherein these devices are installed in close proximity. In any event, their implementation is separate, namely that no mechanical element, intervening in the carrying out of one of these functions, intervenes in the carrying out of the other of these functions. To illustrate this circumstance, among others, China Patent Publication No. CN 102 444 336 will be cited.

A device for opening a plugging and sliding door, involving a worm screw, a set of sun wheels, and an engine fixed in a central position, has been further proposed, by WO 2005/103 429. Stopping the door from being actuated, is achieved by the intermediary of ratchets, able to block the door, in cooperation with a satellite wheel door. This itself is connected to a set of wheels, connected to the engine. The possibility of an emergency opening is briefly mentioned, by using the aforementioned set of wheels. However, this possibility is not substantiated further. In conclusion, this document brings no constructive solution that can be used effectively by a skilled person.

SUMMARY

In view of the above, an aim of embodiments is to remedy, at least partially, the disadvantages of the state of art mentioned above.

Embodiments are to propose a multi-functional module which is likely to integrate different functions connected to the implementation of a plugging and sliding door, such as a door of the type of disclosed in French Patent Publication No. FR-A-3 003 887.

Embodiments are to propose such a multi-functional module, which is considerably compact.

Embodiments are to propose such a multi-functional module, which enables to reliably fulfill the aforementioned functions.

Embodiments are to propose such a multi-functional module, which enables to ensure additional functions, in comparison with the solutions of the state of the art.

In accordance with embodiments, at least one of the aims above is achieved via a multi-functional module for a plugging and sliding door of a transport vehicle, and particularly, for a tram, trolley or train door, said door being mobile between open and closed positions, and said vehicle comprising a mechanism for locking said door in the closed position thereof.

In accordance with embodiments, said multi-functional module is to fulfill both a first function of stopping said door from being actuated, and a second function of opening said door in an emergency.

In accordance with embodiments, the multi-functional module comprises: a crankcase configured to be fixed on a first structural part, connected to the assembly of the vehicle, and particularly, a fixed beam of the drive mechanism of said door; a shaft arranged on the crankcase, the shaft including a first shaft element and a second shaft element which is coaxial with said first shaft element, each one of the first shaft element and the second shaft element being configured to rotate around the main axis thereof on the crankcase, the first shaft element and the second shaft element each having a single degree of free rotation relative to the shared main axis, forming the main shaft axis; a door stop device configured to prevent actuation of the door and cooperate with the first shaft element so as to prevent the passage of the door from the closed position thereof to the open position thereof, and therefore, fulfill a first function of preventing actuation of said door; and an emergency opening device configured to cooperate with the second shaft element so as to unlock the locking mechanism of said door, and therefore fulfill the second emergency opening function of said door.

In accordance with embodiments, the multi-functional module comprises a shaft composed of two shaft elements, of which each one is more specifically dedicated to at least one respective function. More specifically, the rotating of one of the shaft elements enables an emergency opening of the door, whereas the rotating of the other of these elements enables prevention of actuation of the door.

In accordance with embodiments, given that the two shaft elements are arranged in immediate spatial proximity, this gives a very satisfactory compactness to the module. Moreover, the implementation of the module is particularly simple for a user. Thus, it typically involves an intuitive movement on an actuation body of the handle type.

In accordance with embodiments, the spatial proximity between the two shaft elements gives an additional advantage to the module. Thus, the module is likely to fulfill additional functions other than the functions of an emergency opening and stopping the door from being actuated. This is to be compared with the state of the art, in which known devices are only able to ensure an emergency opening and stopping the door from being actuated. Indeed, given that these state of the devices are simply juxtaposed, they do not benefit from any common mechanical interaction.

In accordance with embodiments, an optional feature may include one of the first shaft element and the second shaft element is arranged in a central position on the crankcase and forms an axle, whereas the other one of the first shaft element and the second shaft element is hollow and forms a hub which is arranged on the periphery of said axle.

In accordance with embodiments, an optional feature may include that the axle is arranged, at longitudinal ends thereof, on two assembly parts belonging to said crankcase, whereas the hub only extends over one part of said axle between the two assembly parts.

In accordance with embodiments, an optional feature may include an adjustment device configured to adjust a common angular position of the two shaft elements.

In accordance with embodiments, an optional feature may include an angular adjustment device comprising an angular adjustment body, advantageously having an adjustable size, the angular adjustment body being supported by the emergency opening device and rotating between an inactive position and an active position in which it abuts the crankcase.

In accordance with embodiments, an optional feature may include that one of said shaft elements comprises at least one finger configured to move interior at least one groove arranged in the other of said shaft elements.

In accordance with embodiments, an optional feature may include that the door stop device comprises a first door stopper body connected, at least rotating, to said first shaft element, the door stopper body rotating between an inactive position and an active position in which it cooperates with a second door stopper body fixed on a second structural part, plugging in relation to the assembly of the vehicle, and particularly on a mobile beam of the drive mechanism of said door.

In accordance with embodiments, an optional feature may include that the first stopper body comprises a cam that has at least one radially-moveable section or region, and a second stopper element extending substantially along the main axis of said shaft from said moveable section, in the direction of the interior of the door.

In accordance with embodiments, an optional feature may include that the second stopper element comprises an adjustment screw configured to adjust the size thereof along the main axis of said shaft.

In accordance with embodiments, an optional feature may include that the second stopper body comprises a threaded rod configured to extend into a threading of the cam, a locking nut, and an adjustment screw configured to adjust the size thereof along the main axis of said shaft.

In accordance with embodiments, an optional feature may include an index device configured to index the cam and the second stopper element in relation to the crankcase, in the inactive position thereof and/or in the active position thereof.

In accordance with embodiments, an optional feature may include that the index device comprises at least one orifice of the second stopper element, wherein an indexing element is configured to enter a push-button (of a ball-type) arranged on the crankcase.

In accordance with embodiments, an optional feature may include a detection device comprising contacts configured to detect an indexing of the second stopper element and/or the inlet of emergency opening device in their respective active positions, the contacts being configured to communicate with a control system of said vehicle.

In accordance with embodiments, an optional feature may include a blocking device configured to block the second stopper element, i.e., to prevent movement of the second stopper element from the inactive position thereof to the active position thereof, when the door is in an open state.

In accordance with embodiments, an optional feature may include that the blocking device comprises a blocking element such as a pin which is fixed on an additional stopper element, the blocking device extending along the main axis of the shaft in the direction of the interior of the door.

In accordance with embodiments, an optional feature may include that the additional stopper body comprises a support configured to be fixed on said second structural part so that it may be removed, said support defining a flat spot configured to cooperate with said cam and second stopper element.

In accordance with embodiments, an optional feature may include an actuator body comprising a handle configured to permit actuation by a user of the first shaft element.

In accordance with embodiments, an optional feature may include a drive device configured to drive the door stop device, by the emergency opening device, specific for moving the door stop device under the force of a movement of the emergency opening device.

In accordance with embodiments, an optional feature may include that the drive device comprises at least one finger of one of the shaft elements specific for coming into proximity with a drive wall of the other of the shaft elements when the door stop device is in an active position.

In accordance with embodiments, an optional feature may include the drive wall is one of the walls of a groove and, in the active position of the door stop device, the axis of the finger forms a first angle in relation to this drive wall, the first angle of between 1° and 10°, and particularly, approximately 3°. Whereas in the rest position of door stop device, the axis of the finger forms a second angle in relation to the opposite wall, the second angle of between 5° and 30°, and particularly, approximately 20°.

In accordance with embodiments, an optional feature may include the emergency opening device comprises at least one first pulley as a control pulley which is configured for rotatable connection to said second shaft element, each control pulley being connected to a control body, specific for actuation by a user; and at least one second pulley as a transmission pulley configured for rotatable connection to said second shaft element, said transmission pulley being specific for actuating an unlocking element of a cable type, specific for unlocking said locking mechanism of said door.

In accordance with embodiments, an optional feature may include that the first stopper element for the angular adjustment device comprises a threaded rod extending into a tread of one of said pulleys; a locking nut; and a screw configured to adjust the main size of the first stopper element.

In accordance with embodiments, an optional feature may include a return device configured to return each control pulley and each transmission pulley to a respective rest position.

In accordance with embodiments, an optional feature may include that the return device comprises a spring having coiling arranged around the hub, the spring having a first end configured for connection to the crankcase and a second end configured for rotatable connection to the hub.

These additional characteristics can be implemented with the main above object, individually or in any technically compatible combination.

Embodiments relate to a transport vehicle, such as, for example, a train, tram or trolley, comprising a body, at least one plugging and sliding door, a drive unit for said door, as well as at least one multi-functional module as above defined.

In accordance with embodiments, advantageously, an optional feature of the transport vehicle is that the drive unit comprises a fixed beam configured for connection to the assembly of the vehicle; and a mobile beam configured for connection to a door panel. The emergency opening device and the cam and second stopper device to stop the door from being actuated, are arranged on the fixed beam, whereas the additional stopper body is arranged on the mobile beam.

DRAWINGS

Embodiments will be illustrated by way of example in the drawings and explained in the description below.

DESCRIPTION

Figure 1:
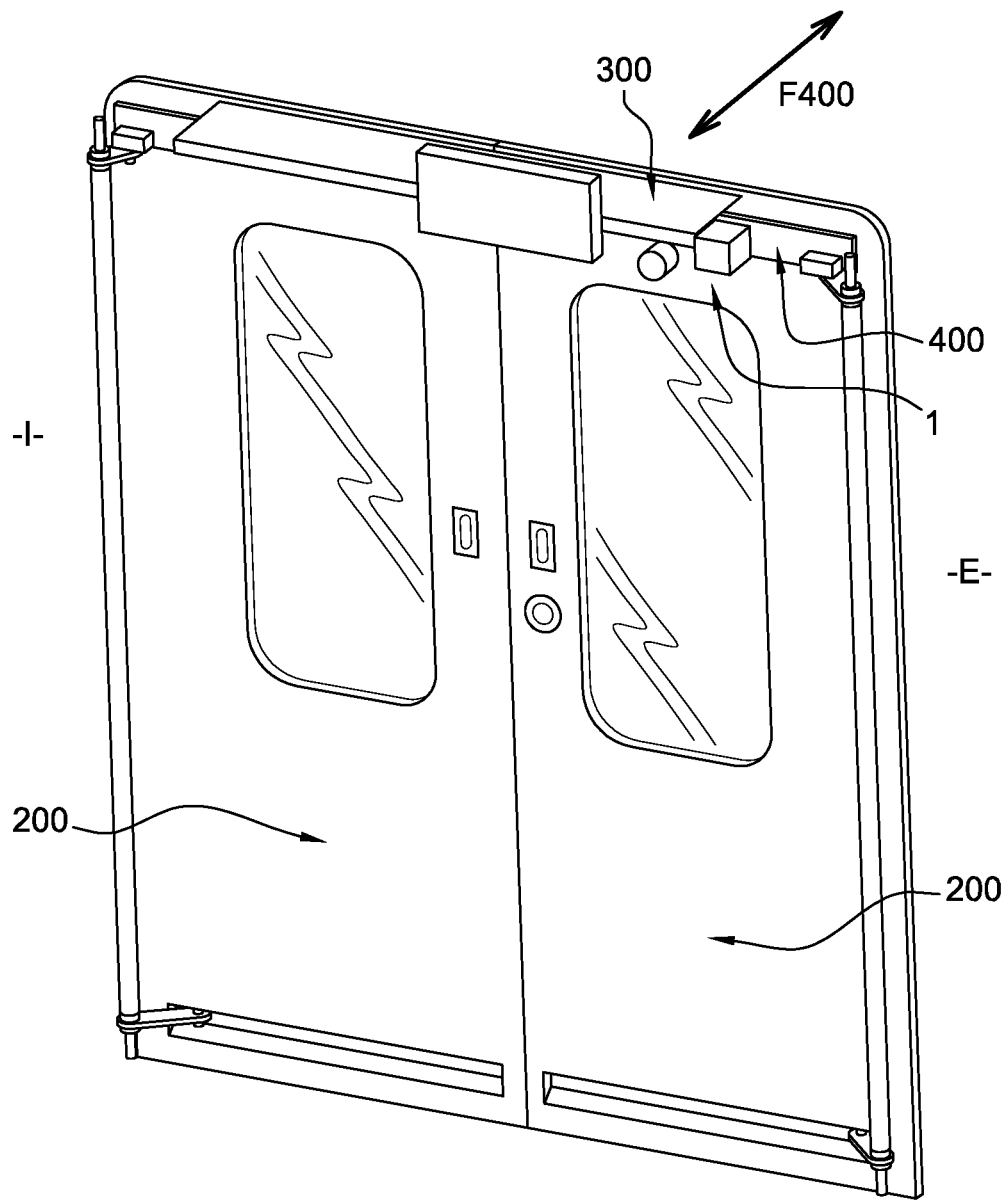
FIG. 1 illustrates a perspective view of a multi-functional module for a plugging and sliding door of a transport vehicle, in accordance with embodiments.

The appended figures illustrate a multi-functional module 1 intended to equip a plugging and sliding door 1 intended to equip a transport vehicle, such as, for example, a tram, a trolley, or a train. The door is known as such, such that it will not be defined in detail below. It is comprised, and particularly, of at least one panel 200, in this case, two panels 200 in the example represented, as well as a mechanism enabling the movement of each panel 200. Such a mechanism comprises, and particularly, a fixed beam 300 connected to the assembly, as well as a mobile beam 400 connected to the suspension of the panels 200. The mobile beam 400 is to plug in relation to the fixed door, according to the double arrow F400 in FIG. 1, using an engine device (not illustrated). In all illustrations, I represents the interior of the vehicle and E represents the exterior of the vehicle.

In accordance with embodiments, the module 1 first comprises a crankcase 100 having an extended crankcase body 101 forming a wall of which the main size extends transversally in relation to the vehicle. The main size defines a main module axis Al of the module 1, of which it will be noted that it is substantially perpendicular to the main direction of the vehicle, corresponding to the advancement of the vehicle. Two flanges 102 and 103, mutually perpendicular, extend towards the bottom from the bottom face of the wall 101, turned towards the interior I of the vehicle. The crankcase 100 further comprises a board 104, whereon the wall 101 is fixed so that it may be removed. The board 104 extends from a base 105, itself connected onto the fixed beam 300 (See, and particularly, FIGS. 2 to 4).

The module 1 further comprises a main shaft, which is an essential mechanical body, as it enables several functions to be carried out, as will be seen below. The shaft is formed of two shaft elements, namely a solid central shaft element 2 forming an axle, as well as a peripheral shaft element 3 forming a hub, and which is arranged concentrically around the central shaft element 2.

The central shaft element 2 extends between the flange 102 and the base 105, which form assembly parts for the central shaft element 2. To this end, the two ends of the central shaft element 2 enter into some orifices, arranged in the two mechanical parts. The central shaft element 2 is journaled, namely that it has a single degree of rotating freely around the main shaft axis A2 thereof relative to both the flange 102 and the base 105. The main shaft axis A2 is parallel to the main module axis A1. Moreover, the central shaft element 2 is connected forward in relation to the flange 102 and to the base 105.

Figure 2:
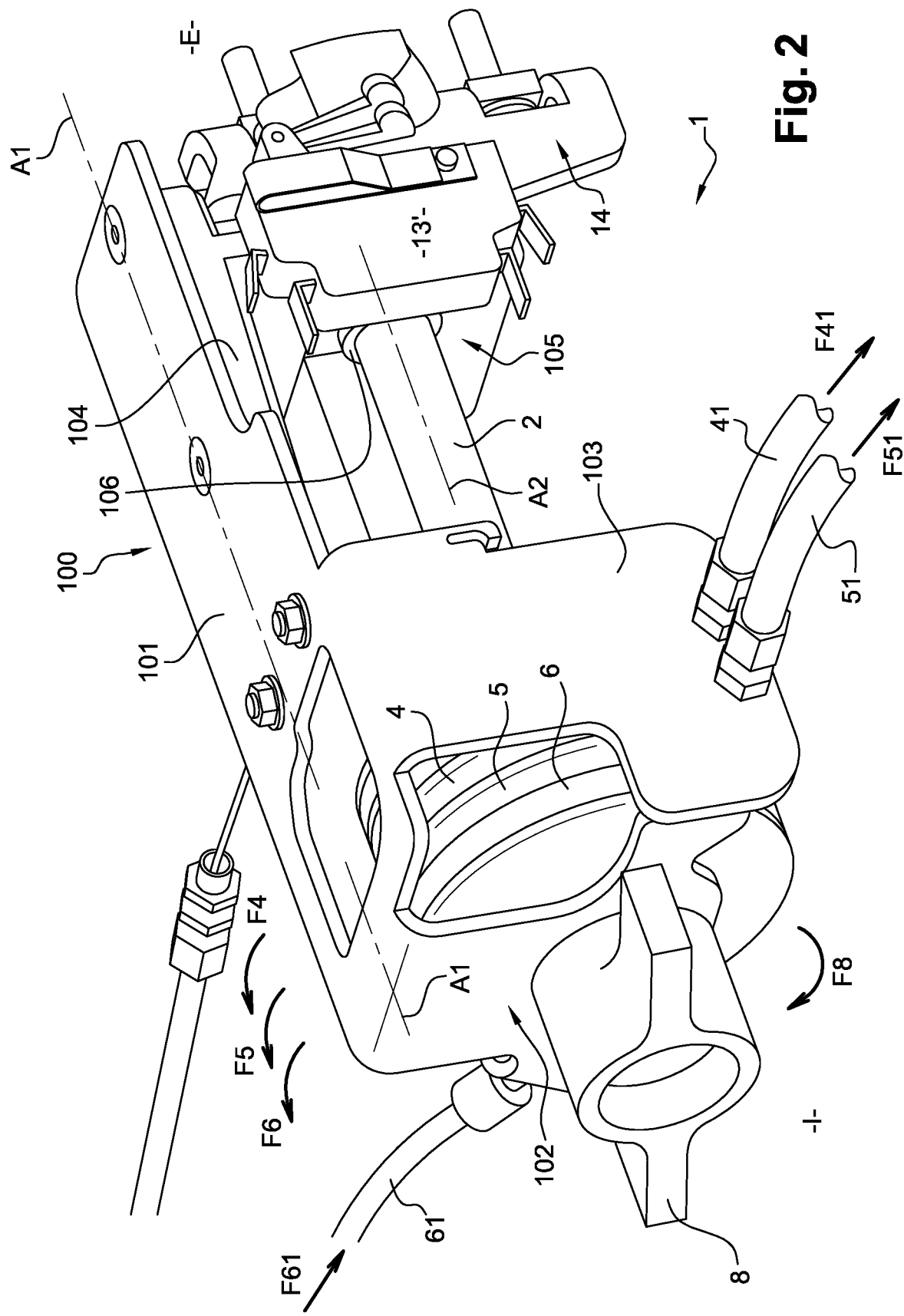
FIG. 2 illustrates a perspective view of the multi-functional module of FIG. 1, from an interior of the vehicle.
Figure 3:
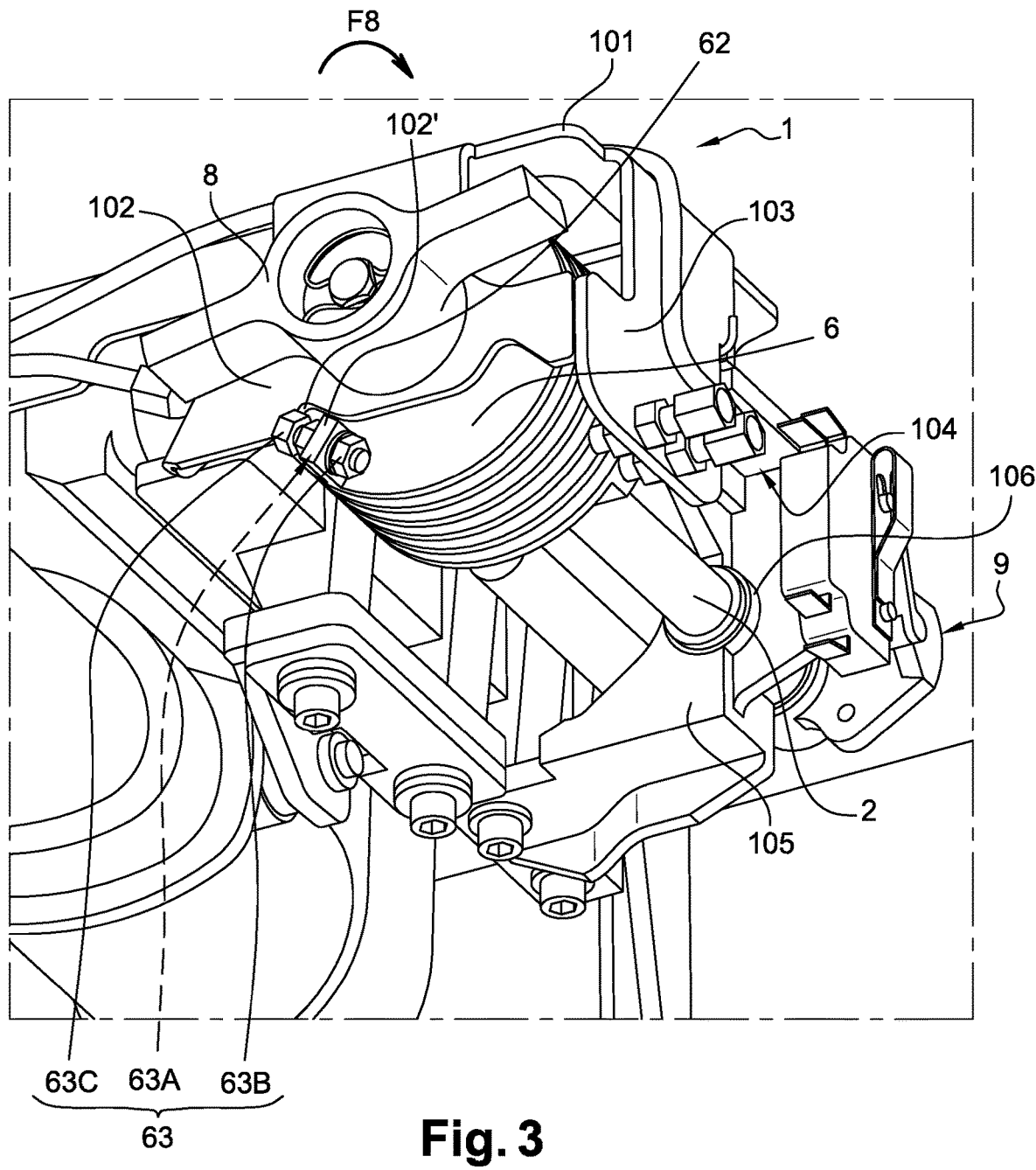
FIG. 3 illustrates a perspective view of the multi-functional module of FIG. 1, from an interior of the vehicle.

As illustrated in FIGS. 2 and 3, to this end, a suitable-type blocking device is provided, for example, a flat spot 106 arranged on the base 105. In the median section thereof, located between the flange 102 and the base 105, the central shaft element 2 is equipped with at least one radial finger 21, 21', in this case, two fingers diametrically opposed, of which the function will be explained below.

Figure 4:
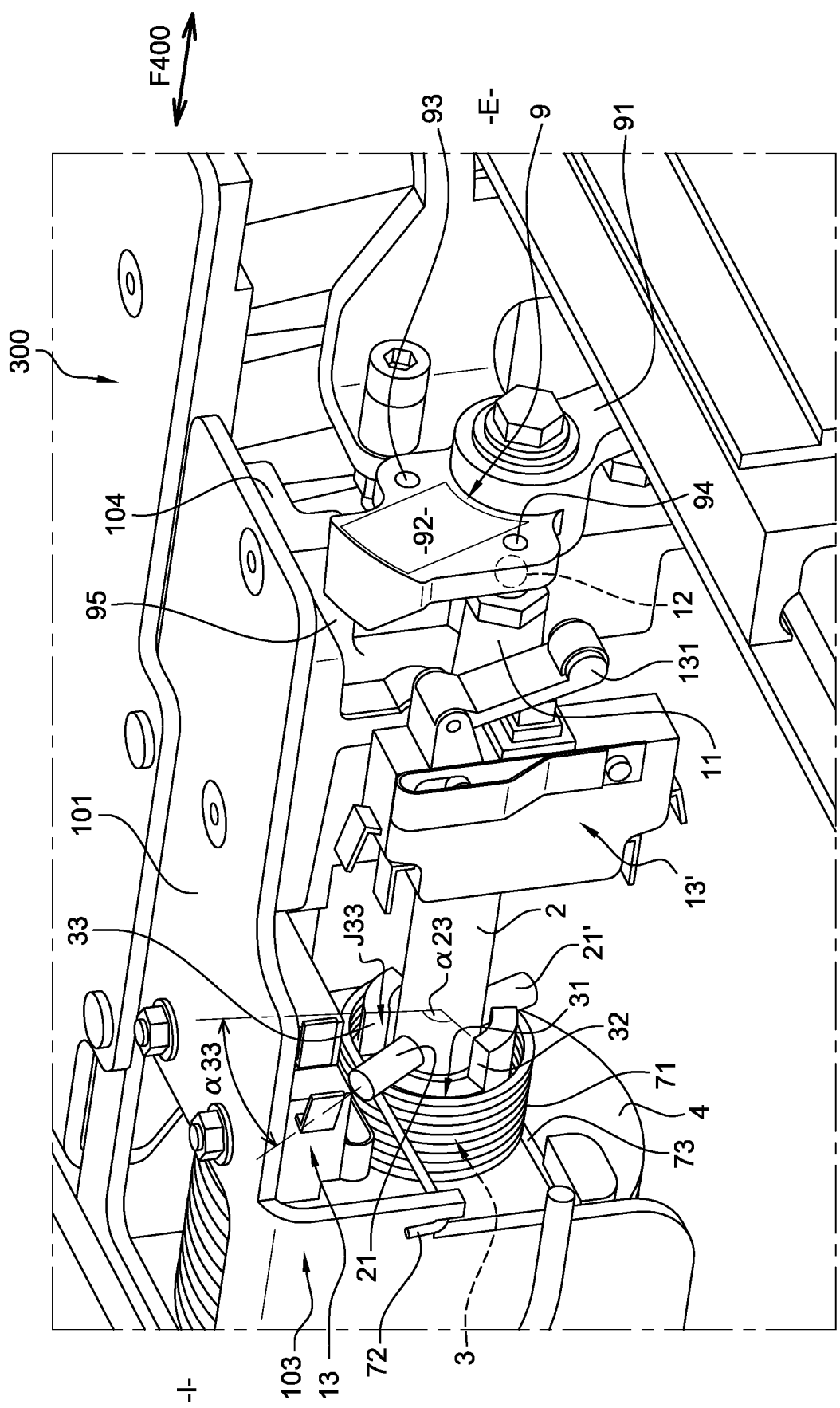
FIG. 4 illustrates a perspective view of the multi-functional module of FIG. 1, from an exterior of the vehicle, and in a rest position.
Figure 5:
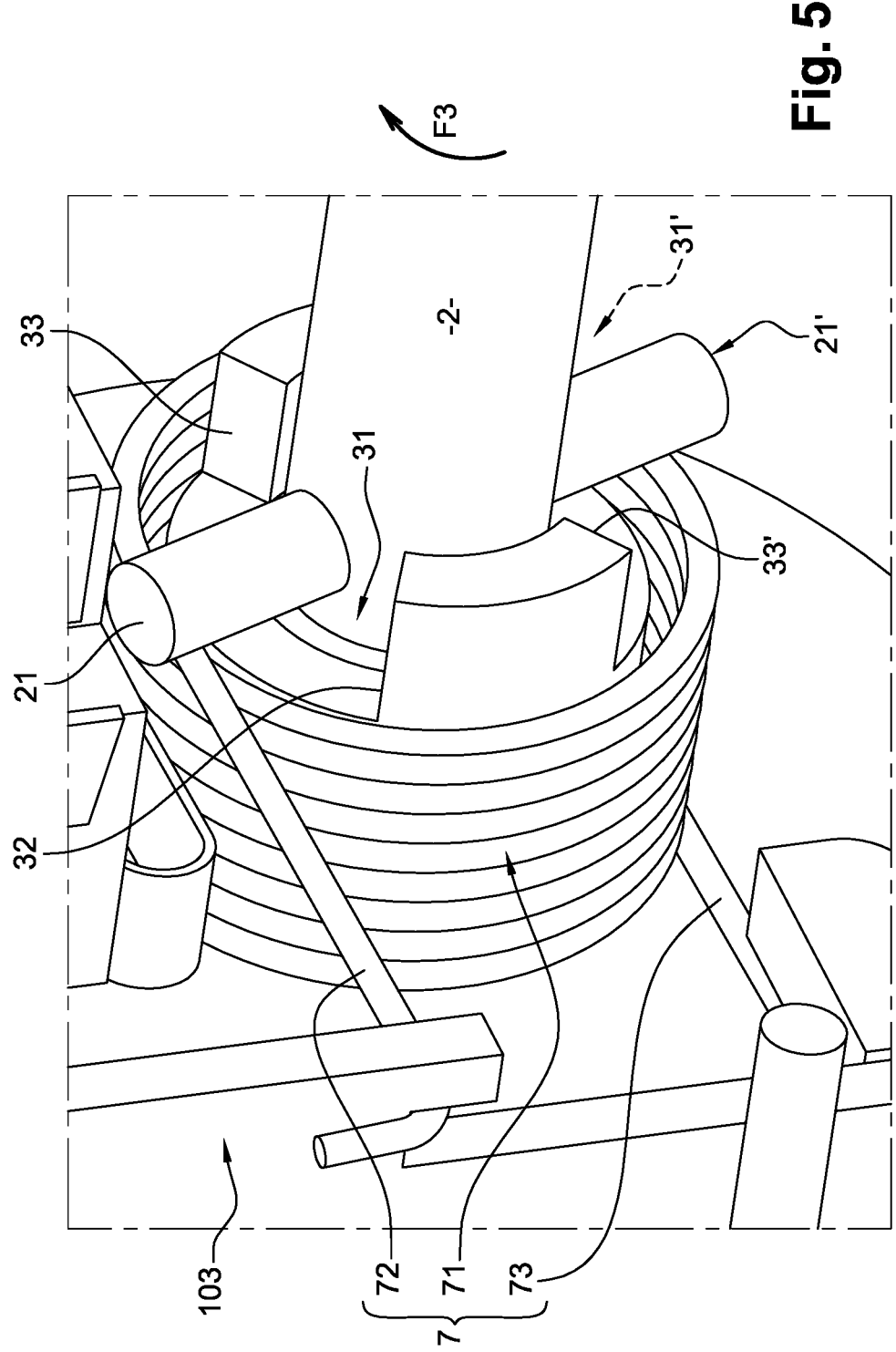
FIG. 5 illustrates a perspective view of the relative position of an axle and a hub of the multi-functional module of FIG. 1, during an emergency opening of the door.

As illustrated in FIGS. 4 and 5, the peripheral shaft element 3 or hub is arranged around the bottom section of the central shaft element 2 adjacent to the flange 102. The peripheral shaft element 3 has a main peripheral shaft axis A3 which is combined with the axis A2, such that, in other words, it is coaxial to the axle 2. The peripheral shaft element 3 is connected to the central shaft element 2 moving forward, along two opposite directions. To this end, the flange 102 blocks the first end of the peripheral shaft element 3 in a first direction, whereas the fingers 21 and 21' block the second end of the peripheral shaft element 3 in the other direction. Moreover, the peripheral shaft element 3 has a single degree of rotating freely in relation to the central shaft element 2, around their common main axis A2, A3.

The first end of the peripheral shaft element 3, adjacent to the interior flange 102, supports a plurality of pulleys 4, 5 and 6. First, the peripheral shaft element 3 is to support two control pulleys 4, 5, (i.e., drive or lead pulleys), each pulley 4, 5 connected to a respective cable 41, 51, both represented schematically. These cables 41, 51 are each connected to control bodies (not illustrated), such as handles provided respectively on the interior I and exterior E of the door. Moreover, the peripheral shaft element 3 is to support a transmission pulley 6 (i.e., driven or led pulley), which is connected to an additional cable 61, represented schematically. The cable 61 is to cooperate with a device (not illustrated), in a manner known per se, enabling the door to be unlocked.

The pulleys 4, 5, and 6 are interconnected to each other, while also being connected to the peripheral shaft element 3. In other words, there is no degree of freedom between the pulleys 4, 5, and 6, and the peripheral shaft element 3, such that a rotating movement of one of these mechanical parts leads to the rotating of the other parts. It will be noted, that in the example illustrated, the drive pulleys 4, 5 are arranged side-by-side, whereas the driven pulley 6 is positioned on the exterior side of one of the drive pulleys 4, 5. As a variant (not illustrated), the driven pulley 6 may be inserted between the drive pulleys 4, 5.

As illustrated in FIG. 3, the pulley 6 supports a thread 62 deepened by a threading. Moreover, a first stopper element 63 is provided to extend transversally to the main module axis Al and tangentially to the rotation of the pulley 6. The first stopper element 63 comprises a threaded rod 63A extending into the aforementioned threading, a locking nut 63B, and an adjustment screw 63C. The screw 63C enables modification of the overall length (i.e., the main size) of the first stopper element 63 along a tangential axis to the rotation of the pulley 6. In use, the screw 63C is likely to abut the walls of an indentation 102' arranged in the flange 102.

As illustrated in FIG. 4, the bottom face of the wall 101 supports a contact 13 equipped with a mobile element (not illustrated). The mobile element is to cooperate, in a manner known per se, with a boss (not illustrated) arranged on the pulley 4. The contact 13 is to be connected to the control system (not illustrated) of the vehicle.

The opposite end of the peripheral shaft element 3, adjacent to the exterior flange 103, is deepened by at least one groove 31, 31', in this case two grooves in the example illustrated. As will be seen below, in accordance with embodiments, each finger 21, 21' moves angularly in relation to the walls opposite the grooves 31, 31', respectively 32, 33, as well as 32', 33'. Thus, the walls 33, 33' are able to form stoppers for each finger 21, 21' of the central shaft element 2, in a configuration which will be defined below. The peripheral shaft element 3 is, moreover, surrounded by the coiling 71 of a spring 7, of which a first end 72 is connected to the crankcase 100, and of which the other end 73 is connected to the pulley 4. As will be seen below, the spring 7 is to return the mechanical elements from the module 1 to the rest position of the module 1.

At the interior end thereof, turned towards the flange 102, the axle 2 is fixed to a handle 8, enabling the rotating thereof by a user who is present in the vehicle. At the opposite exterior end thereof, turned towards the flange 103, the axle 2 is, moreover, fixed to a cam 9. The central shaft element 2 is connected for rotational and longitudinal movement, on the one hand with the handle 8 and, on the other hand, with the cam 9, by any suitable means known per se.

As illustrated in FIGS. 4, 6, 7, and 10, the cam 9 has two moveable or active regions 91, 92, which are mainly diametrically opposite to each other. The first active region 91 supports a second stopper element 10 which extends in the direction of the interior of the vehicle substantially along the axis A2.

Figure 8:
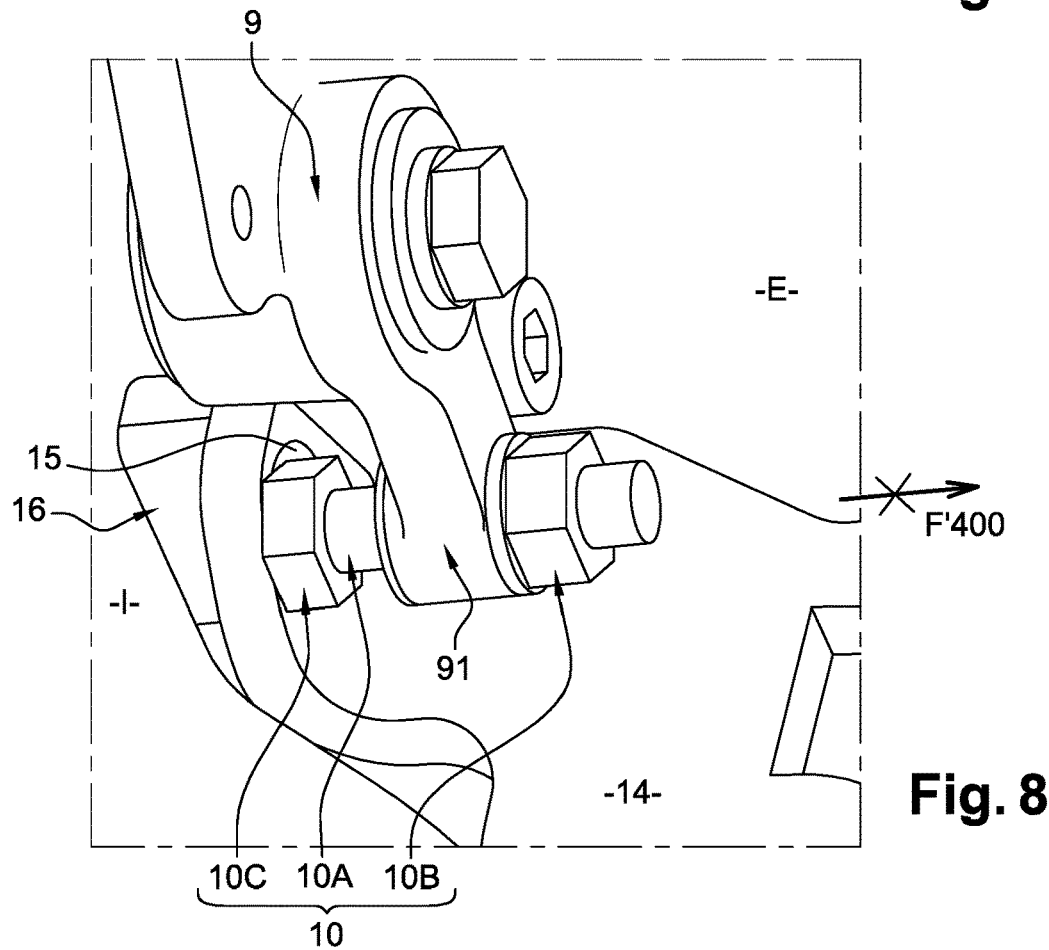
FIG. 8 illustrates a perspective view of the multi-functional module of FIG. 1 in the position thereof of stopping the actuation of the door.

As illustrated in FIG. 8, the second stopper element 10 comprises a threaded rod 10A extending into a threading of the active region 91, a locking nut 10B, and an adjustment screw 10C. The screw 10C enables the length (i.e., the size) of the stopper element 10 to be modified along the axis A2. Moreover, the active region 92 opposite the cam 9 is first deepened by two indexing orifices 93, 94. It further comprises a boss 95 which protrudes in the direction of the interior of the vehicle substantially along the axis A2.

Different additional functional parts moreover equip the crankcase 100 of the module 1. First, a push-button 11 is arranged on the crankcase 100. The push-button 11 is equipped with a spring to repel a ball 12 in the direction of the cam 9, namely towards the exterior of the vehicle. In addition, a second contact 13' equipped with a mobile element 131, is arranged on the crankcase 100. The contact 13' is connected to the control system (not illustrated) of the vehicle.

Figure 6:
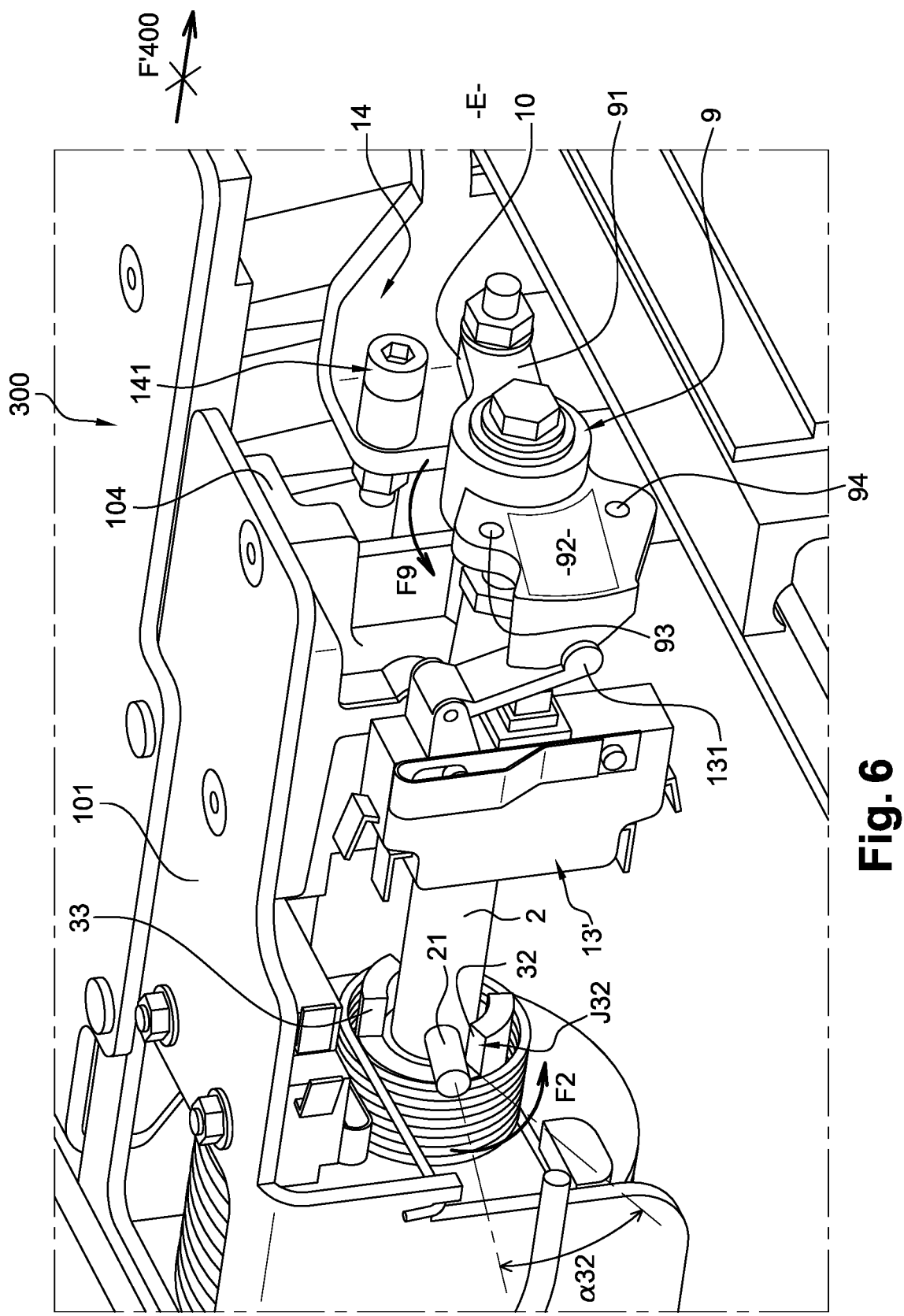
FIG. 6 illustrates a perspective view of the multi-functional module of FIG. 1, in a position thereof of stopping the actuation of the door.
Figure 10:
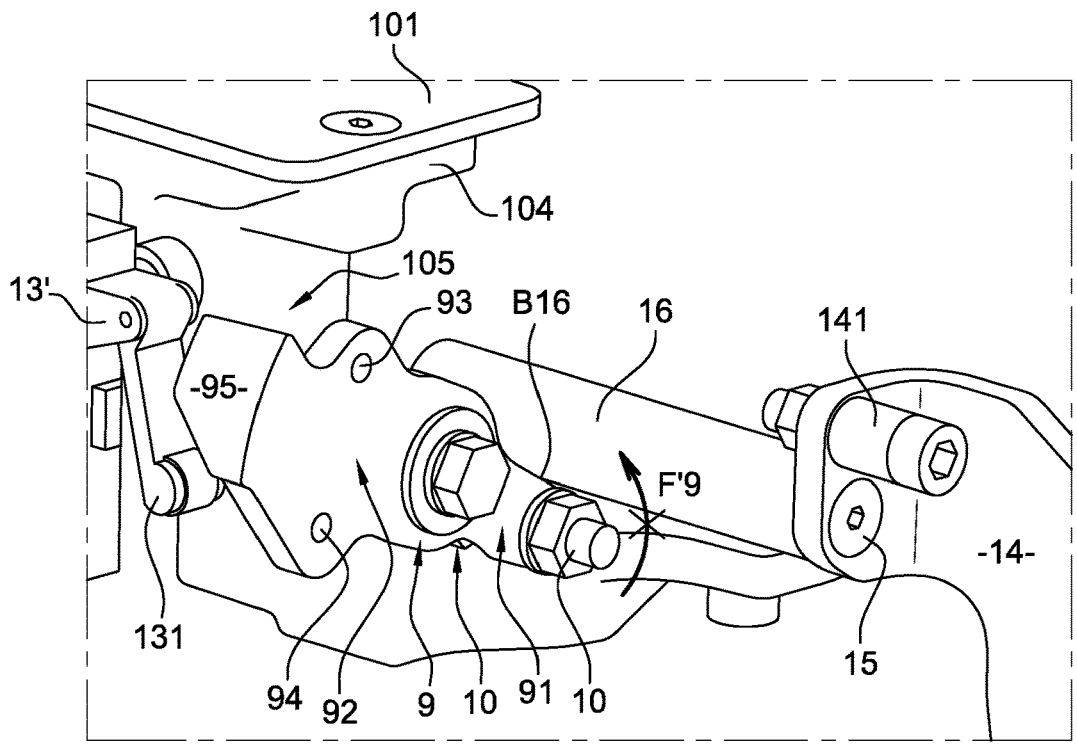
FIG. 10 illustrates a perspective view of the multi-functional module of FIG. 1 from the exterior, and in a position to prevent the stopping of the door from being actuated when the door has been opened beforehand.

As illustrated in FIGS. 6 and 10, a support 14 is fixed on the mobile beam 400 in any suitable manner. In accordance with embodiments, the fixing of the support 14 may be a type that is removeable, and particularly, by screwing, for example, using at least one screw 141 arranged in FIGS. 4, 6, and 10.

As illustrated in FIGS. 8 and 10, the support 14 defines a flat spot 15 for abutting the second stopper element 10 supported by the cam 9. In accordance with embodiments, the unit formed by the cam 9 and the second stopper element 10 is to form a stopper body, which is specific for cooperating with an additional stopper body formed by the support 14 and the flat spot 15. The support 14 is additionally equipped with a pin 16 which extends axially opposite from the flat spot 15, that is towards the interior I of the door. As will be seen below, the pin 16 is intended to block the passage from the stopper element 10 to the active position thereof.

In accordance with embodiments, the implementation of the module 1, such as defined above, will now be explained below. The explanation will, and particularly, highlight the different functionalities, permitted by the module 1.

In a normal functioning of the vehicle, the spring 7 is to return the pulleys 4, 5, and 6 into their respective rest positions. Given that the peripheral shaft element 3 is rotateably connected to the pulleys 4, 5, and 6, the spring 7 extends to repel the wall 33 of the groove 31 in the direction of the finger 21 supported by the central shaft element 2. Such a movement, however, is limited by the first stopper element 63. Indeed, the position of the screw 63C is adjusted such that it abuts the walls opposite the indentation 102' before the wall 33 contacts the finger 21. Therefore, there is a functional gap $J_{33}$ (See, FIG. 4) between the wall 33 and the finger 21. The angle $\alpha_{33}$ between the axis of the finger 21 and the surface 33 (See FIG. 4) is typically between 5° and 30°, and particularly, approximately 20°.

In accordance with embodiments, no other significant mechanical action is exerted on the shaft elements 2, 3, which are mainly immobile. Consequently, the shaft elements 2, 3 do not interfere with the overall functioning of the vehicle, just like the different mechanical parts which are connected to them. The cable 61 supported by the pulley 6 does not prevent the free activation of the door locking unit. In addition, the second stopper element 10 connected to the cam 9 is not positioned opposite the flat spot 15, defined by the support 14 arranged on the mobile beam 400. The cam 9 is moreover indexed, namely held in place in this inactive position, since the ball 12 enters into the housing defined by the orifice 94. The mobile beam 400 is free to move in relation to the fixed beam 300, which is materialized by the arrow F400 in FIG. 4. Under these conditions, the free opening of the door is not impeded.

First, it is assumed that an emergency opening of the door is desired to be carried out, equipped with the module 1 in accordance with embodiments. In this case, a user, for example, a passenger or a crew member, actuates the handle connected to one of the control pulleys 4, 5. This actuation leads to a movement forward of the cable 41 or cable 51, according to the arrows F41 or F51 in FIG. 2, then a corresponding rotation of all three pulleys 4, 5, and 6, according to the arrows F4 to F6. Finally, the rotating of the transmission pulley 6 leads to the movement forward of the cable 61 which itself is connected, according to the arrow F61, which enables the unlocking of the door. At the end of this emergency opening movement, the boss supported by the pulley 4 cooperates with the contact 13, which then transmits the corresponding information to the control system (not illustrated) of the vehicle.

During the rotation of the pulleys 4, 5, and 6, the peripheral shaft element 3 is also driven rotating according to the arrow F3 in FIG. 5. It will be noted that, during this movement of the pulleys 4, 5, and 6 and of the peripheral shaft element 3, the central shaft element 2 remains fixed such that the peripheral shaft element 3 turns freely around the central shaft element 2. As illustrated in FIG. 5, from the rotation of the peripheral shaft element 3, each finger 21, 21' is located near the second wall 32, 32' of each groove 31, 31'. It will consequently be noted that, the free movement of the peripheral shaft element 3 is not impeded by an untimely abutment of the fingers 21, 21' against these walls 32 and 32'. To this end, a skilled person will use his general knowledge to assign a suitable value to the angle $\alpha_{31}$ formed by the opposite walls 32 and 33 of the groove 31.

It is now assumed that it is desired to stop the door from being actuated, which typically comes about when the control system of the vehicle does not deliver clear information, according to which the door is closed and locked. In this case, a user actuates the control handle 8, by rotating according to the arrow F8 in FIG. 2, namely clockwise in the example illustrated. This rotation leads to a corresponding rotation of the axle 2, according to the arrow F2, as well as of the cam 9, according to the arrow F9. The finger 21 then leaves the initial position thereof, near the first wall 33, but however distant from the first wall 33, to move in the direction of the opposite wall 32 (see FIG. 6). It will be noted that, during the initial phase of moving the cam, the ball 12 of the push-button 11 is freed from the first orifice 94, arranged in this cam 9. A skilled person will adjust the force of the spring of the push-button 11, such that, on the one hand, this freeing operation may be implemented without any inconsiderate force by a user, and that, on the other hand, the ball 12 firmly holds the cam 9 in position during the normal functioning of the vehicle.

At the end of the rotating movement of the cam 9, the second orifice 93 comes opposite the push-button 11. The spring equipping the push-button 11 then repels the ball 12 into the housing, defined by this orifice 93. The cam is consequently held in place, in other words, indexed in this active position, which is represented, and particularly, in FIG. 7. Under these conditions, a rotation in the direction opposite to the cam 9, enabling it to be brought back into the original inactive position thereof in FIG. 4, is prevented, except for exerting a significant mechanical force. An example of such a significant force will be defined below, to illustrate one of the additional functionalities of embodiments.

Figure 7:
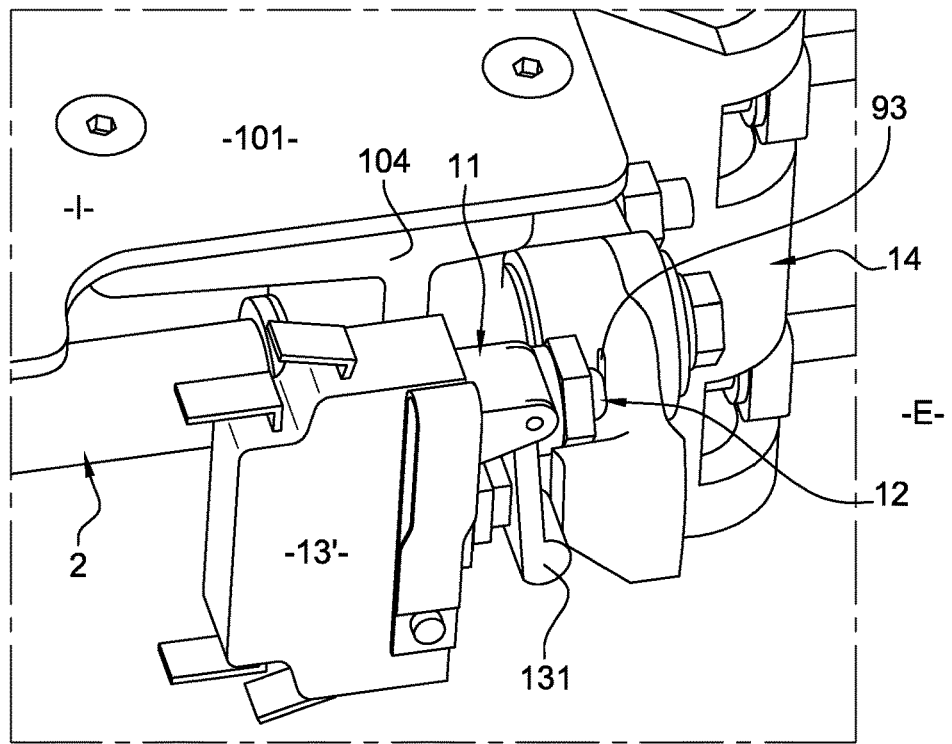
FIG. 7 illustrates a perspective view of the multi-functional module of FIG. 1 in a position thereof of stopping the actuation of the door.

As illustrated in FIGS. 7 and 8, the second stopper element 10 is in an active position thereof, opposite the flat spot 15. In other words, the second stopper element 10 is found in the extension of the flat spot 15 along the axis A2. Consequently, the mobile beam 400 cannot be moved towards the exterior in relation to the fixed beam 300, which is materialized by the struck-out arrow F'400 in FIGS. 6 and 8. Under these conditions, any attempt to open the door is prevented. It will be noted that, the screw 10C enables adjustments to the length of the second stopper element 10 such that the second stopper element 10 is substantially contacting the flat spot 15 in this active position. Under these conditions, any significant movement of the door is prevented.

In the active position of the cam 9, the boss 95 of the cam 9 is to cooperate with the contact 13', which may then transmit the corresponding information to the control system of the vehicle. In this active position, the finger 21 is in the immediate proximity of the wall 32, while however being separate from the wall 32, as to enable a free movement of the finger 21 during the action of stopping the door from being actuated. The gap between the finger and the surface 32, referenced J32 in FIG. 6, is adjusted by action on the screw 63C of the first stopper element 63. The first stopper element 63 therefore is to form an angular adjustment between the central shaft element 2 and the peripheral shaft element 3. The angular gap is fixed to obtain an angle $\alpha_{32}$ between the axis of the finger 21 and the surface 32, typically between 1° and 10°, and particularly, approximately 3°. The angle $\alpha_{32}$ is visible in FIG. 6, where it is illustrated with an exaggerated amplitude with the aim of being clearer.

It will be noted that, if a user rotates the handle 8 according to an insufficient amplitude, so that the cam 9 comes into the active position thereof, there is then no indexing of the ball 12 in the orifice 93. In this case, an additional return device (not illustrated) may advantageously be provided, to return the cam 9 into the rest position thereof, when the active position thereof is not reached.

It will be noted that, conforming with a particularly advantageous characteristic of embodiments, the module 1 may fulfill at least one other additional emergency opening function, and function of stopping the door from being actuated defined above.

Thus, embodiments first enables an unlocking, known as emergency unlocking of the door, when actuation of the door is stopped. In this position of stopping actuation of the door, as explained above in reference, and particularly, to FIG. 6, the finger 21 is found near the second wall 32 of the groove 31. A user may then actuate the handle 8 connected to one of the control pulleys 4 and 5, similarly to what has been defined above in reference to the emergency opening of the door.

Figure 9:
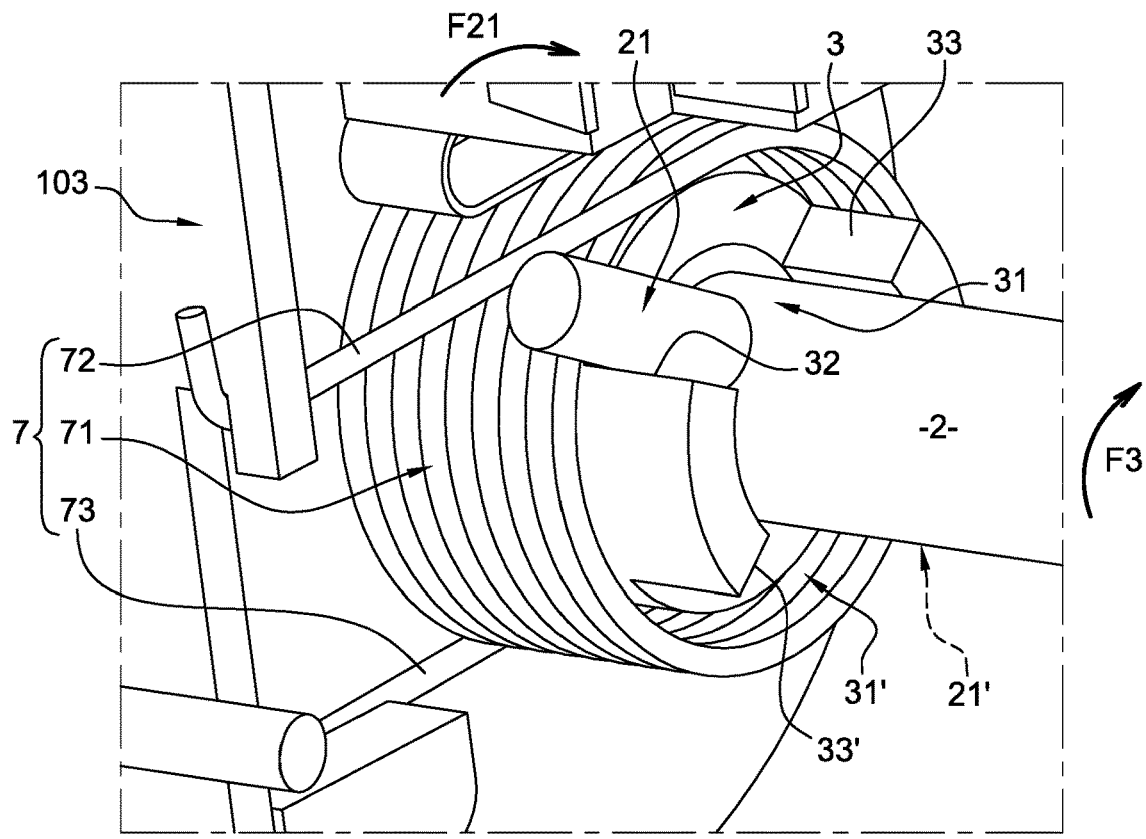
FIG. 9 illustrates a perspective view of the relative position of the axle and the hub during an opening of the door, when the door has been stopped from being actuated beforehand.

As shown in FIG. 9, during rotation of the peripheral shaft element 3 according to the arrow F3, the wall 32 of the groove 31 abuts the finger 21 and thus exerts, on the finger 21, a force directed towards the top of this figure. This then drives the finger 21 in rotation according to the arrow F21 and, consequently, the central shaft element 2 as well as the cam 9. The cam 9 leaves the active position thereof, such that the second stopper element 10 is no longer opposite the additional flat spot 15, such that the free opening of the door is again permitted. During the initial movement phase of the cam 9, the ball 12 of the push-button 11 is freed from the orifice 93 arranged in the cam 9. The movement of the ball 12 is carried out in a similar manner to the freeing of the ball exterior of the other orifice 94, defined in reference to FIG. 6.

As illustrated in FIG. 10, an additional function, known as forbidding the stopping of the actuation of the open door, ensured by the module 1 in accordance with embodiments. As illustrated, the door of the vehicle is open or ajar, such that the mobile beam 400 is moved forward towards the exterior in relation to the fixed beam 300, compared with the position in FIG. 4. It is thus assumed, that a user wants to stop the door from being actuated, in this position of opening. The user may actuate the handle 8, which rotates the axle 2 and the cam 9, in a similar manner to what has been defined above. At an intermediate stage of this rotation, however, the cam 9 abuts the pin 16, which is materialized by the reference B16. The rotating movement cannot consequently be followed to position the cam 9 in the active position thereof in FIG. 6, which is materialized by the struck-out arrow F'9. The pin 16 ensures the blocking of the cam 9 to give the module 1 a function of preventing the stopping of an actuation of the door when the door is in the open position.

In the example defined and represented, the central shaft element 2 and the peripheral shaft element 3 have a common degree of rotating freely, around their common main axis A2, A3. The angular articulation between the two parts is limited, however, because of the cooperation between the finger 21 and the walls of the groove 31. As a non-represented variant, it may be provided that the central shaft element 2 has no such finger, such that the movement thereof is uncoupled from that of the peripheral shaft element 3. In this variant, the module 1 does not enable the function of the emergency unlocking of the door being stopped from being actuated to be carried out. It ensures, however, the functions of emergency opening, stopping the door from being actuated, as well as preventing the stopping of actuation of the open door, while benefiting from a significant constructive simplicity.

The term "coupled" or "connected" may be used herein to refer to any type of relationship, direct or indirect, between the components in question, and may apply to electrical, mechanical, fluid, optical, electromagnetic, electromechanical or other connections. In addition, the terms "first," "second, etc. are used herein only to facilitate discussion, and carry no particular temporal or chronological significance unless otherwise indicated.

This written description uses examples to disclose the invention, including the preferred embodiments, and also to enable any person skilled in the art to practice the invention, including making and using any devices or systems and performing any incorporated methods. The patentable scope of embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, may be mixed and matched by one of ordinary skill in the art to construct additional embodiments and techniques in accordance with principles of this application.

LISTING OF REFERENCE SYMBOLS

1 Module
2 Axle
3 Hub
4 Pulley
5 Pulley
6 Pulley
7 Spring
8 Handle
9 Cam
10 2nd stopper element
10A Threaded rod of 2nd stopper element
10B Locking nut of 2nd stopper element
10C Adjustment screw of 2nd stopper element
11 Push-button
12 Ball of push-button
13 1st contact
13' 2nd contact
14 Support
15 Flat spot of support
16 Pin
21 1st axle finger
21' 2nd axle finger
31 1st hub groove
31' 2nd hub groove
32 1st Wall of 1st hub groove
32' 1st Wall of 2nd hub groove
33 2nd Wall of 1st hub groove
33' 2nd Wall of 2nd hub groove
41 Cable
51 Cable
61 Cable
62 Tread
63 1st stopper element
63B Locking nut of 1st stopper element
63A Threaded rod of 1st stopper element
63C Adjustment screw of 1st stopper element
71 Coiling of spring
72 1st end of spring
73 2nd end of spring
91 1st active region of cam
92 2nd active region of cam
93 1st orifice of cam
94 2nd orifice of cam
95 Boss of cam
100 Crankcase
101 Crankcase body
102 1st crankcase flange
102' Indentation of 1st crankcase flange
103 2nd crankcase flange
104 Board
105 Base
106 Flat spot of base
131 Mobile element of 2nd contact
141 Screw
200 Panels
300 Fixed beam
400 Mobile beam
F400 Movement direction of mobile beam
F'400 Movement direction of mobile beam
A1 Axis of module
A2 Axis of axle
A3 Axis of hub
I Interior of the vehicle
E Exterior of the vehicle
α31 Angle of 1st hub groove α32 Angle between 1st axle finger and 1st Wall of 1st hub groove α33 Angle between 1st axle finger and 2nd Wall of 1st hub groove J32 Gap between 1st axle finger and 1st Wall of 1st hub groove J33 Gap between $1^{st}$ axle finger and $2^{nd}$ Wall of $1^{st}$ hub groove

What is claimed is:

1. A module for a door of a vehicle, the door having a drive mechanism and the vehicle having a locking mechanism to enable movement of the door between an open position and a closed position, the module comprising:
a crankcase configured to be fixed on a fixed beam of the drive mechanism;
a shaft operatively connected to the crankcase, the shaft including a first shaft element and a second shaft element that is coaxial with the first shaft element, the first shaft element and the second shaft element being arranged for rotation about a common shaft axis to have a single common degree of free rotation;
a door actuator stop device operatively connected to the first shaft element, and configured to prevent actuation of the door and thereby prevent passage of the door from the closed position to the open position;
an emergency opening device operatively connected to the second shaft element, and configured to unlock the locking mechanism and enable passage of the door from a closed position to an open position.

2. The module of claim 1, wherein:
the first shaft element is arranged in a central position on the crankcase and forms an axle, and
the second shaft element is hollow and forms a hub arranged at a periphery of the axle.

3. The module of claim 1, further comprising an angular adjustment device configured to adjust a common angular position of the first shaft element and the second shaft element.

4. The module claim 3, wherein the angular adjustment device comprises a stopper element having a first stopper body configured for adjustment in length and supported by the emergency opening device for rotation between an inactive position and an active position to thereby contact the crankcase.

5. The module claim 4, wherein the door actuator stop device comprises a second stopper body connected for rotatable connection to the first shaft element between an inactive position and an active position, where the second stopper body is to cooperate with a third stopper body fixed to a mobile beam of the drive mechanism of the door.

6. The module claim 5, wherein the second stopper body comprises a cam having at least one radially-moveable section and a stopper element extending substantially along the shaft axis from said at least one moveable section, in a direction of an interior of the door.

7. The module claim 5, further comprising an index device configured to index the second stopper body relative to the crankcase, in an inactive position of the second stopper body.

8. The module claim 7, further comprising a detection device configured to detect an indexing of at least one of the second stopper body and the emergency opening device in an active position, respectively.

9. The module claim 5, further comprising a blocking device configured to block the second stopper body and thereby prevent movement of the second stopper body from the inactive position to the active position when the door is in an open position.

10. The module claim 5, wherein the third stopper body comprises a support removably attached to the mobile beam, said support defining a flat spot configured to cooperate with said second stopper body.

11. The module claim 1, further comprising a drive device configured to drive the door actuator stop device between the active position to the inactive position under a force of movement of the emergency opening device.

12. The module claim 11, wherein the drive device comprises at least one finger of the first shaft element configured to move into proximity of a drive wall of the second shaft elements when the door actuator stop device is positioned in the active position.

13. The module claim 1, wherein the emergency opening device comprises:
at least one first pulley as a control pulley configured for rotatable connection to the second shaft element and connection to a control body, that is configured for actuation by a user, and
a second pulley as a transmission pulley configured for rotatable connection to the second shaft element to enable actuation of an unlocking element configured to unlock the locking mechanism of the door.

14. The module claim 13, further comprising a return device configured to return the at least one control pulley and the transmission pulley to a respective rest position.

15. A vehicle, comprising:
a vehicle body;
at least one door having a drive mechanism;
a locking mechanism to enable movement of the at least one door between an open position and a closed position; and
at least one module including:
a crankcase configured to be fixed on a fixed beam of the drive mechanism;
a shaft operatively connected to the crankcase, the shaft including a first shaft element and a second shaft element that is coaxial with the first shaft element, the first shaft element and the second shaft element being arranged for rotation about a common shaft axis to have a single common degree of free rotation;
a door actuator stop device operatively connected to the first shaft element, and configured to prevent actuation of the door and thereby prevent passage of the door from the closed position to the open position; and
an emergency opening device operatively connected to the second shaft element, and configured to unlock the locking mechanism and enable passage of the door from a closed position to an open position.

16. The vehicle of claim 15, wherein the vehicle comprises one of a train, a tram, or a trolley.

17. A vehicle door, comprising:
at least one panel;
a drive mechanism for the at least one panel;
a locking mechanism to enable movement of the at least one panel between an open position and a closed position; and
at least one module including:
a crankcase configured to be fixed on a fixed beam of the drive mechanism;
a shaft operatively connected to the crankcase, the shaft including a first shaft element and a second shaft element that is coaxial with the first shaft element, the first shaft element and the second shaft element being arranged for rotation about a common shaft axis to have a single common degree of free rotation;

a door actuator stop device operatively connected to the first shaft element, and configured to prevent actuation of the door and thereby prevent passage of the door from the closed position to the open position; and an emergency opening device operatively connected to the second shaft element, and configured to unlock the locking mechanism and enable passage of the door from a closed position to an open position.

\* \* \* \* \*